United States Patent
DiCarlo (10) Patent No.: US 10,675,117 B2
(45) Date of Patent: Jun. 9, 2020

(54) MATCHING SURGICAL DISPLAY TECHNOLOGIES USING VIRTUAL PRIMARIES

(71) Applicant: Intuitive Surgical Operations, Inc., Sunnyvale, CA (US)

(72) Inventor: Jeffrey M. DiCarlo, Austin, TX (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 16/074,921

(22) PCT Filed: Feb. 10, 2017

(86) PCT No.: PCT/US2017/017353
§ 371 (c)(1),
(2) Date: Aug. 2, 2018

(87) PCT Pub. No.: WO2017/139563
PCT Pub. Date: Aug. 17, 2017

(65) Prior Publication Data
US 2019/0029771 A1    Jan. 31, 2019

Related U.S. Application Data (60) Provisional application No. 62/294,939, filed on Feb. 12, 2016.

(51) Int. Cl.
*G06T 1/20*   (2006.01)
*H04N 1/60*   (2006.01)
(Continued)

(52) U.S. Cl.
CPC .............. *A61B 90/37* (2016.02); *A61B 90/00* (2016.02); *G06T 1/20* (2013.01); *H04N 1/6052* (2013.01);
(Continued)

(58) Field of Classification Search
CPC combination set(s) only.
See application file for complete search history.

(56) References Cited

U.S. PATENT DOCUMENTS 5,579,031 A  *  11/1996  Liang ........................ G06F 3/13
                                                            345/604
2004/0174389 A1 *  9/2004  Ben-David .......... G09G 3/3413
                                                            345/694
(Continued)

FOREIGN PATENT DOCUMENTS

| EP | 2672712 A1 | 12/2013 |
| EP | 2928176 A2 | 10/2015 |
| WO | WO-2015143671 A1 | 10/2015 |

OTHER PUBLICATIONS

International Preliminary Report on Patentability for Application No. PCT/US2017/017353, dated Aug. 23, 2018, 10 pages.
(Continued)

*Primary Examiner* — Wesner Sajous (57) ABSTRACT

A virtual primaries transform controller maps a color of a first pixel in a scene received from an imaging pipeline to a color of a second pixel, which is displayed on a monitor. The first color and the second color are the same color. The direct mapping performed by the controller assures that the colors of pixels displayed using two different display technologies are identical.

21 Claims, 4 Drawing Sheets

(51) Int. Cl.
  *H04N 9/67* (2006.01)
  *H04N 9/64* (2006.01)
  *A61B 90/00* (2016.01)
  *A61B 34/37* (2016.01)

(52) U.S. Cl.
  CPC .............. *H04N 1/6058* (2013.01); *H04N 9/67* (2013.01); *A61B 34/37* (2016.02); *A61B 2090/372* (2016.02)

(56) References Cited

U.S. PATENT DOCUMENTS

| | | | |
|---|---|---|---|
| 2010/0302439 A1* | 12/2010 | Le | H04N 9/67 348/453 |
| 2013/0050245 A1 | 2/2013 | Longhurst et al. | |
| 2013/0063496 A1* | 3/2013 | Basler | G09G 3/003 345/690 |
| 2015/0092090 A1 | 4/2015 | Miura | |
| 2015/0287354 A1* | 10/2015 | Wang | G09G 3/2051 345/598 |
| 2016/0029925 A1 | 2/2016 | Kuramoto et al. | |
| 2017/0324887 A1* | 11/2017 | Min | H04N 5/93 |

OTHER PUBLICATIONS

International Search Report and Written Opinion for Application No. PCT/US2017/017353, dated May 1, 2017, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP17750821.5 dated Aug. 9, 2019, 10 pages.

* cited by examiner

MATCHING SURGICAL DISPLAY TECHNOLOGIES USING VIRTUAL PRIMARIES

RELATED APPLICATIONS

This patent application is the U.S. national phase of International Patent Application No. PCT/US2017/017353, filed Feb. 10, 2017, which designated the U.S. and which claims priority to and the benefit of U.S. Provisional Patent Application No. 62/294,939, entitled "MATCHING SURGICAL DISPLAY TECHNOLOGIES USING VIRTUAL PRIMARIES," filed Feb. 12, 2016, each of which is incorporated by reference herein in its entirety.

BACKGROUND

Field of the Invention

The present invention relates generally to display devices, and more particularly to matching colors on display devices using different display technologies.

Description of Related Art

Surgical system 100 is a computer assisted surgical system that includes an endoscopic imaging system 192, a surgeon's console 194 (master), and a patient side support system 110 (slave), all interconnected by wired (electrical or optical) or wireless connections 197. One or more electronic data processors may be variously located in these main components to provide system functionality. Examples are disclosed in U.S. Patent Application Publication No. US 2008/0065105 A1, which is incorporated by reference herein.

Patient side support system 110 includes an entry guide manipulator 130. At least one surgical device assembly is coupled to entry guide manipulator 130. Each surgical device assembly includes either an instrument that in turn includes either a surgical instrument or an image capture unit. For example, in FIG. 1, one surgical device assembly includes an instrument 135-1 with a shaft 137-1 and an image capture unit that extends through entry guide 115 during a surgical procedure. Instrument 135-1 is sometimes referred to as an endoscope, or alternatively as an imaging system device or camera instrument. Typically, entry guide 115 includes a plurality of lumens.

Imaging system 192 performs image processing functions on captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Surgeon's console 194 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

Figure 1:
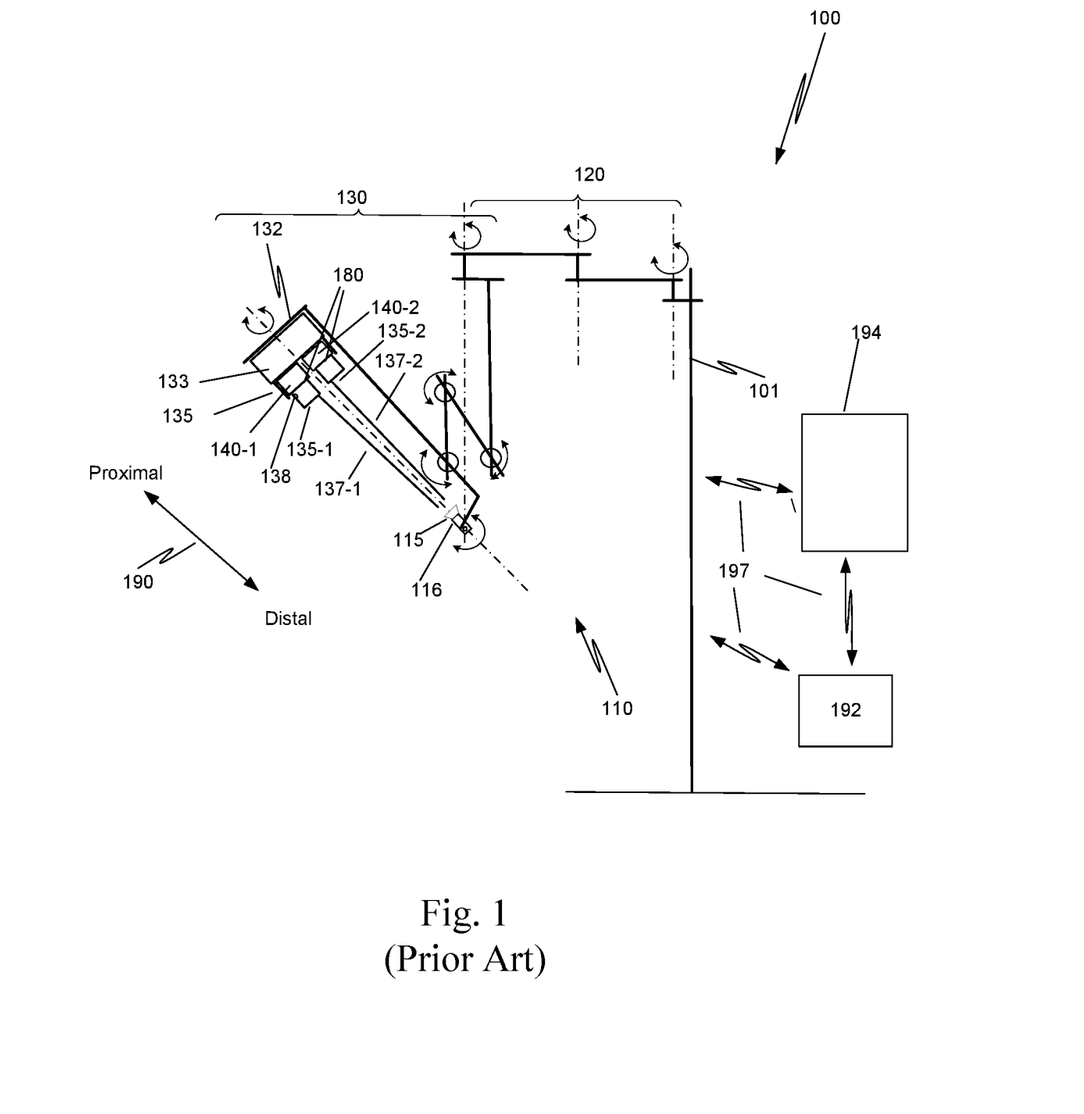
FIG. 1 is an illustration of a prior-art computer-assisted surgical system.

Base 101 of patient side support system 110 supports an arm assembly that includes a passive, uncontrolled setup arm assembly 120 and an actively controlled manipulator arm assembly 130. Actively controlled manipulator arm assembly 130 is sometimes referred to as entry guide manipulator 130. An entry guide manipulator assembly platform 132, sometimes referred to as platform 132, is coupled to a distal end of fourth manipulator link 119. An entry guide manipulator assembly 133 is rotatably mounted on platform 132. Arrow 195 shows the distal and proximal directions.

Entry guide manipulator assembly 133 includes an instrument manipulator positioning system. Entry guide manipulator assembly 133 rotates a plurality of instrument manipulators 140-1, 140-2 as a group around axis 125.

Each of a plurality of instrument manipulators 140-1, 14-2 is coupled to entry guide manipulator assembly 133 by a different insertion assembly 136. In one aspect, each insertion assembly 136 is a telescoping assembly that moves the corresponding instrument manipulator away from and towards entry guide manipulator assembly 135. In FIG. 1, each of the insertion assemblies is in a fully retracted position.

Each of the plurality of instrument manipulator assemblies 140-1, 140-2 includes a plurality of motors that drive a plurality of outputs in an output interface of that instrument manipulator. See U.S. Patent Application No. 61/866,115 (filed on 15 Aug. 2013), which is incorporated by reference, for one example of an instrument manipulator and a surgical instrument that can be coupled to the instrument manipulator.

Each of plurality of surgical device assemblies 180 includes a different one of the plurality of instrument manipulator assemblies and an instrument including one of a surgical instrument and an image capture unit. Each of instruments 135-1, 135-2 includes a body that houses a transmission unit. The transmission unit includes an input interface including a plurality of inputs. Each of instruments 135-1, 135-2 also includes a shaft 137-1, 137-2 sometimes referred to as a main tube that extends in the distal direction from the body. An end effector is coupled to a distal end of the shaft of a surgical instrument assembly, and an image capture unit, e.g., a camera, is included in a distal end of a different surgical instrument assembly. See U.S. Patent Application No. 61/866,115 (filed on 15 Aug. 2013), which is incorporated by reference, for one example of an instrument manipulator assembly and a surgical instrument.

Each of instruments 135-1, 135-2 is coupled to the instrument mount interface of a corresponding instrument manipulator assembly 140-1, 140-2 so that a plurality of inputs in an input interface of the transmission unit in instrument 135-1, 135-2 are driven by plurality of outputs in the instrument mount interface of instrument manipulator assembly 140-1, 140-2. See U.S. Patent Application No. 61/866,115 (filed on 15 Aug. 2013).

As shown in FIG. 1, the shafts of plurality of surgical device assemblies 180 extend distally from bodies of the instruments. The shafts extend through a common cannula 116 placed at the entry port into the patient (e.g., through the body wall or at a natural orifice). In one aspect, an entry guide 115 is positioned within cannula 116, and each instrument shaft extends through a channel in entry guide 115, so as to provide additional support for the instrument shafts.

A monitor in surgeon's console 194 is a liquid crystal display (LCD) that is backlit with cold-cathode fluorescent tubes (CCFLs). This monitor has a good gamut for surgical site scenes, and surgeons have become accustomed to the colors of the surgical site as reproduced on this monitor.

SUMMARY

To assure that scenes displayed on display devices having different display technologies have the same coloring, a first color of a first pixel is directly mapped to a a second color of a second pixel. The second pixel is for display on a second display device having a second display technology. The second color is identical to the first color. The first color of the first pixel is defined by a combination of at least three sub-pixels of first real primary colors of a first display technology. The second color of the second pixel is defined by a combination of at least three sub-pixels of second real primary colors of the second display technology. The second real primary colors are different from the first real primary colors. In one aspect, the second pixel in included in a surgical site scene.

In one aspect, the second color of the second pixel is in a gamut of the second display device. The first color of the first pixel is in a gamut of a first display device, and the first display device has a first display technology that is different from the second display technology. In one aspect, the first display device includes a liquid crystal display monitor backlit with cold-cathode fluorescent tubes. Also, in one aspect, the second display device includes a liquid crystal display monitor backlit by light emitting diodes.

In one aspect, the mapping directly a first color of a first pixel to a second color of a second pixel for display on a second display device having a second display technology includes mapping directly the first color of the first pixel to an identical color of a third pixel in an X-Y-Z color space. The mapping directly a first color of a first pixel to a second color of a second pixel for display on a second display device having a second display technology also includes mapping directly the color of the third pixel in the X-Y-Z color space to an identical color of the second pixel. The identical color of the second pixel being the second color. In one aspect, the mapping directly the color of the first pixel to an identical color of a third pixel in a X-Y-Z color space and the mapping directly the third pixel in the X-Y-Z color space to an identical color of the second pixel are performed together in a single mapping act.

In another aspect, a scene is displayed on a monitor having a display technology. The displayed scene includes a plurality of pixels. Each of the pixels has a color. The color of each of the plurality of pixels being a same color as a color of a corresponding pixel of a corresponding plurality of pixels in the scene when the scene is displayed on a different monitor having a different display technology. In one aspect, the scene is a surgical scene.

In one aspect, the color of each of the plurality of pixels is in a gamut of the display device, and the color of each of the corresponding plurality of pixels is in a gamut of the different display device. In one aspect, the gamut of the different display device is a gamut of a liquid crystal display monitor backlit with cold-cathode fluorescent tubes and the gamut of the display device is a gamut of a liquid crystal display monitor backlit by light emitting diodes.

An apparatus includes a display unit. The display unit includes a virtual primaries transform controller and a display device. The virtual primaries transform controller is configured to receive a plurality of pixels representing a surgical site scene. A first pixel of the plurality of pixels has a first color defined by a first combination of three sub-pixels of first real primary colors. The virtual primaries transform controller is configured to directly map the first color to a second color of a second pixel. The second color of the second pixel is defined by a second combination of three sub-pixels of second real primary colors. The first color and the second color are a same color. The display device is configured to receive the second pixel and to display the second pixel. In one aspect, the second pixel in included in a surgical site scene.

In one aspect, the display device uses a display technology, and the color of the second pixel is in a gamut of the display device. The color of the first pixel is in a gamut of a different display device, and the different display device has another display technology that is different from the display technology of the display device. In one aspect, the different display device includes a liquid crystal display monitor backlit with cold-cathode fluorescent tubes. Also, in one aspect, the display device includes a liquid crystal display monitor backlit by light emitting diodes.

In one aspect, the virtual primaries transform controller being configured to directly map the first color to a second color of a second pixel includes the virtual primaries transform controller being configured to map directly the color of the first pixel to an identical color of a third pixel in an X-Y-Z color space. The virtual primaries transform controller being configured to directly map the first color to a second color of a second pixel also includes the virtual primaries transform controller being configured to map directly the color of the third pixel in the X-Y-Z color space to an identical color of the second pixel. The identical color of the second pixel being the second color. In one aspect, the virtual primaries transform controller being configured to map directly the color of the first pixel to an identical color of a third pixel in an X-Y-Z color space and the virtual primaries transform controller being configured to map directly the color of the third pixel in the X-Y-Z color space to an identical color of the second pixel includes the virtual primaries controller being configured to perform the two mappings as a single direct mapping.

DETAILED DESCRIPTION

A liquid crystal display monitor 196 backlit by cold-cathode fluorescent tubes, which was used in display unit 195 of the prior surgeon's console 194, is being phased out by LCD manufacturers. Thus, liquid crystal display monitor 196 in display unit 195 of surgeon's console 194 and other monitors in a surgical operating theater that utilize a cold-cathode fluorescent tubes backlight are being replaced with, for example, a liquid crystal display monitor backlit by light emitting diodes.

Figure 2:
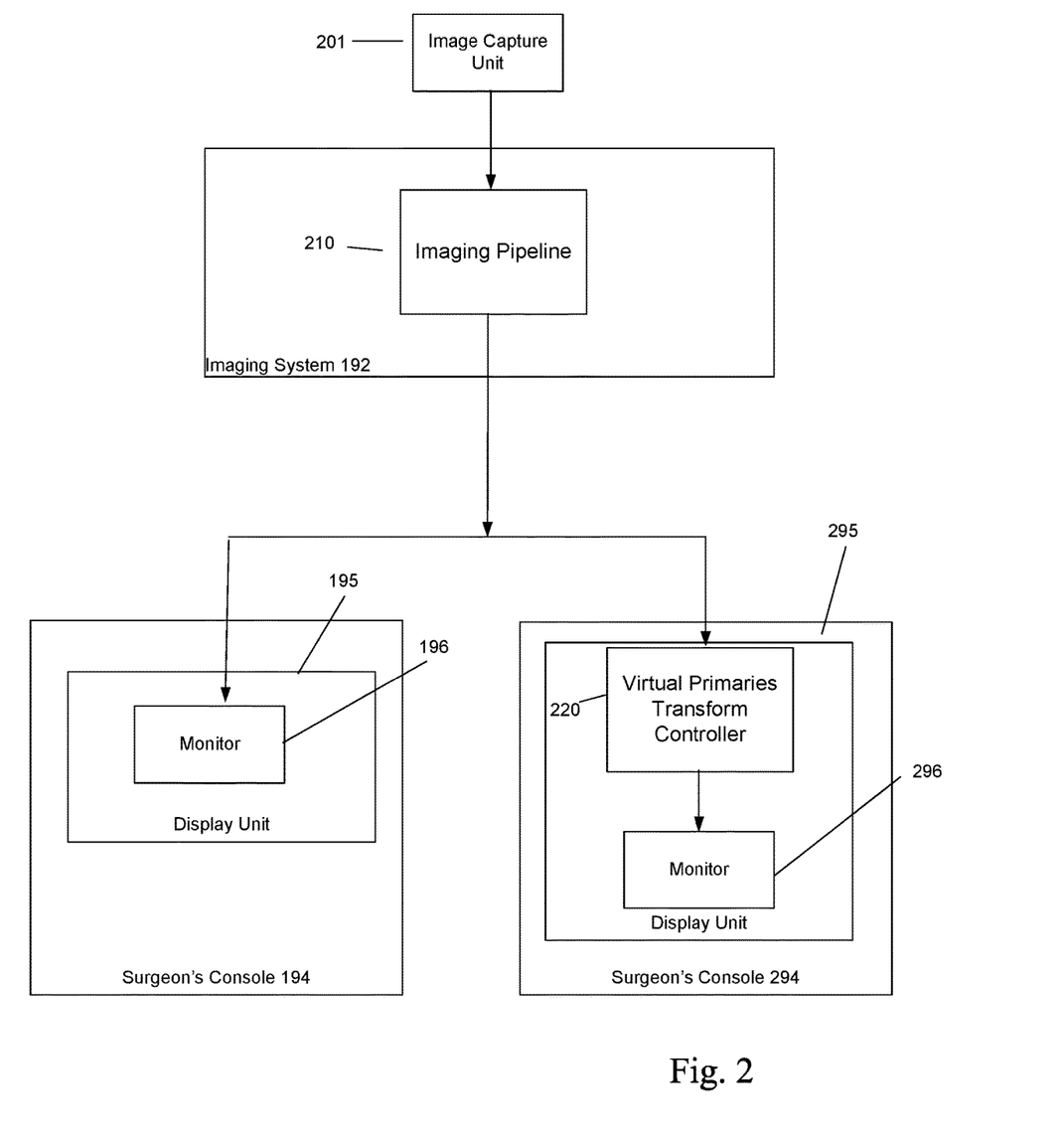
FIG. 2 is a block diagram of parts of a computer-assisted surgical system that includes a display unit with a virtual primaries transform controller.

It is important that the color of surgical scenes displayed on a monitor 296 (FIG. 2) of surgeon's console 294 remains consistent to a surgeon's expectations. Surgeon's console 294 is the same as surgeon's console 194, except monitor 296 uses a display technology that is different from the display technology used by monitor 196. Also, the coupling of two surgeon's consoles to imaging system 192 is illustrative only and is not intended to be limiting. The aspects described below can be implemented in any display unit used to display surgical site scenes as well as any display unit that replaces another display unit with a different display technology and that is used to display images having the characteristics described more completely below. Thus, the use of different display units, as illustrated in FIG. 2, is optional as is the use of more than one monitor. Also, monitors 196 and 296 are examples of display devices.

Changes in the camera, lights, or display technologies that make up surgical imaging systems can dramatically change the color appearance of a displayed surgical scene. In particular, the color of an image reproduced on a liquid crystal display monitor 196, which is backlit by cold-cathode fluorescent tubes, (sometimes referred to as CCFL monitor 196) can be quite different from the color of that same image reproduced on liquid crystal display monitor 296, which is backlit by light emitting diodes, (sometimes referred to as LED monitor 296) due to the difference in the backlights.

Herein, liquid crystal display monitor 196 backlit by cold-cathode fluorescent tubes is an example of a first monitor that utilizes a first display technology. Liquid crystal display monitor 296 backlit by light emitting diodes is an example of a second different monitor that utilizes a second display technology, where the first display technology is different from the second display technology.

In one aspect, a virtual primaries transform controller 220 is included in display unit 295. Virtual primaries transform controller 220 receives the same input pixel data representing a surgical site scene that is displayed on CCFL monitor 196. Virtual primaries transform controller 220 implements a transform that eliminates color differences between surgical site scenes displayed on a liquid crystal display monitor 196 backlit by cold-cathode fluorescent tubes and on a liquid crystal display monitor 296 backlit by light emitting diodes. Specifically, a color of a pixel in a surgical scene displayed on CCFL monitor 196 is identical to, i.e., is the same as, a color of a corresponding pixel in the same surgical scene displayed on LED monitor 296 even though the two monitors utilize different display technologies. Here, pixels at a same location in the two displayed surgical scenes are said to be corresponding pixels.

Virtual primaries transform controller 220, sometimes referred to as controller 220, utilizes a direct mapping that converts primaries color for CCFL monitor 196 to virtual primaries that are displayed by LED monitor 296. This direct mapping assures that a color of a pixel that is displayed on CCFL monitor 196 is the same as the color of a corresponding pixel that is displayed on LED monitor 296. The real primary colors of CCFL monitor 196 are mapped to virtual primaries for LED monitor 296, because the real primary colors of CCFL monitor 196 are different colors from the real primary colors of LED monitor 296, and the real primary colors of CCFL monitor 196 may be outside the gamut of LED monitor 296. The colors produced on LED monitor 296 are formed from combinations of the virtual primaries to assure that the colors displayed on both monitors are identical.

Hence, LED monitor 296 displays the same scene as CCFL monitor 196 without introducing any color differences between the two scenes when viewed by a human. Moreover, this is done without concern for the fact that some colors produced on a liquid crystal display monitor 196 that is backlit by cold-cathode fluorescent tubes cannot be reproduced on liquid crystal display monitor 296 that is backlight by light emitting diodes. The reason is that the colors that cannot be reproduced are not typically found in the scenes of interest, such as surgical site scenes.

This is contrary to prior mappings that have attempted to force the entire range of colors that can be produced using a first display technology to be included in, e.g., overlay, the range of colors that can be produced using the second display technology. This prior mapping result in colors that are not identical due to scaling or other techniques used to overlay the two color ranges. This is in contrast to the direct mapping that produces the same color independent of the display technology. In addition, this is done without any unnatural effects appearing in the displayed scene due to the virtual primaries transformation performed by controller 220.

A portion of the total range of possible colors identifiable by the human eye that can be reproduced by a display device is referred to as a gamut of the display device. The gamut of a display device is less than the total range of colors identifiable by the human eye. A gamut of a display device is commonly represented as an area in an International Commission on Illumination (CIE) 1931 chromaticity diagram 300. CIE 1931 chromaticity diagram 300 is a graphic representation of the total range of colors identifiable by the human eye. Since FIG. 3 is a black and white figure, areas of chromaticity diagram 300 are labeled with colors found in that area.

The CIE 1931 color model defines three primary colors X, Y, and Z. The CIE chromaticity coordinates x and y are shown in FIG. 3, where $x=X/(X+Y+Z)$ and $y=Y/(X+Y+Z)$. It is currently impossible to find three real colors with a gamut containing all visible colors, and so the three primary colors X, Y, and Z are imaginary.

In a liquid crystal display monitor, the display includes vertical and horizontal rows of pixels. Each pixel includes at least three sub-pixels of different real primary colors. Typically, the three sub-pixels of different real primary colors, sometimes referred to as real primaries, are a red sub-pixel, a green sub-pixel and a blue pixel. Through different combinations of light from each of the sub-pixels, each of the pixels can output any color in the gamut of the monitor. As is known, for a given display technology, combination of the real primary colors are used to produce other colors. Thus, the color of a pixel is determined by the combination of the primary colors of the sub-pixels that make up that pixel and the backlight color characteristics.

Figure 3:
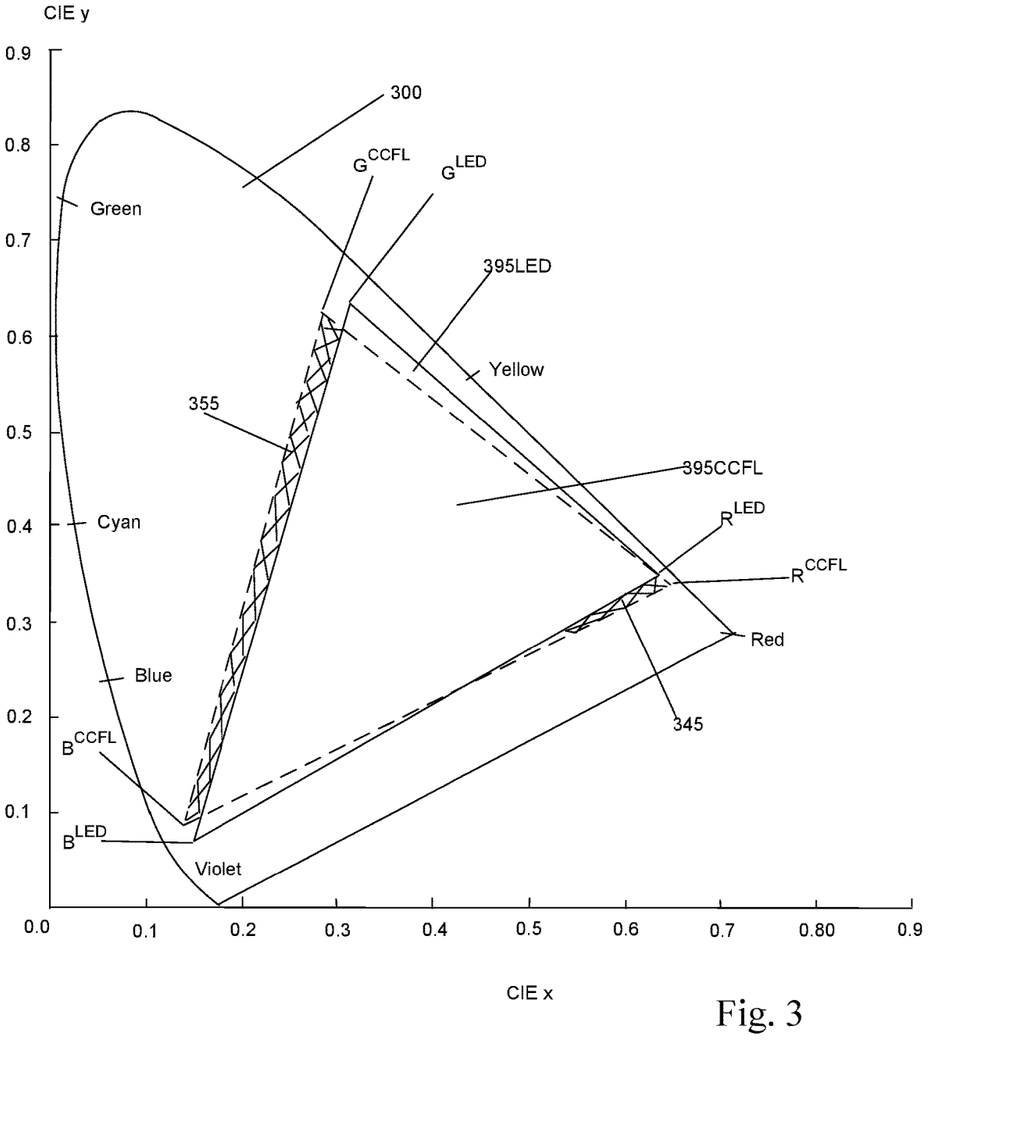
FIG. 3 is an illustration of a CIE 1931 chromaticity diagram that includes gamuts of two display devices with different display technologies.

In FIG. 3, the area within dotted line triangle defines a gamut 395CCFL in the CIE 1931 color model. Gamut 395CCFL is the gamut of liquid crystal display monitor 196 that is backlit by cold-cathode fluorescent tubes.

Similarly, the area within solid line triangle defines a gamut 395LED in the CIE 1931 color model. Gamut 395LED is the gamut of liquid crystal display monitor 296 that is backlit by light emitting diodes.

The vertices of the triangle bounding gamut 395CCFL are colors $R^{CCFL}$, $G^{CCFL}$, and $B^{CCFL}$, which are the real primaries for CCFL monitor 196. The vertices of the triangle bounding gamut 395LED are colors $R^{LED}$, $G^{LED}$, and $B^{LED}$, which are the real primaries for LED monitor 296.

Combinations of primary colors $R^{LED}$, $G^{LED}$, and $B^{LED}$ of LED monitor 296 can produce each color in gamut 395LED. Similarly, combinations of primary colors $R^{CCFL}$, $G^{CCFL}$, and $B^{CCFL}$ of CCFL monitor 196 can produce each color in gamut 395CCFL.

To produce the same color pixel on LED monitor 296 as the color of the corresponding pixel on CCFL monitor 196, a combination of primary colors $R^{CCFL}$, $G^{CCFL}$, and $B^{CCFL}$ of CCFL monitor 196 is used to generate the color of the pixel displayed on LED monitor 296.

However, as shown in FIG. 3, primary colors $R^{CCFL}$, $G^{CCFL}$, and $B^{CCFL}$ of CCFL monitor 196 are different colors from primary colors $R^{LED}$, $G^{LED}$, and $B^{LED}$ of LED monitor 296. Therefore, with respect to LED monitor 296, to produce a second pixel on monitor 296 having the identical color as a first pixel on CCFL monitor 196, the primaries of the LED monitor 296 must match the real primaries of CCFL monitor 196. Because these CCFL real primaries are different than the real primaries of LED monitor 296 and some of these primaries may or may not fall outside the gamut of LED monitor 296, the CCFL real primaries are virtual primaries for LED monitor 296. Virtual primaries refer to any primary that is not the real primary of the monitor.

Two differences are noted between gamut 395CCFL and gamut 395LED. LED monitor 296 cannot produce the intense reds in a first color area 345, as represented by the cross-hatched area, in gamut 395CCFL. Also, LED monitor 296 cannot produce the deep blues and green in a second color area 355, as represented by the cross-hatched area, in gamut 395CCFL. The two cross-hatched areas in FIG. 3 represent undisplayable combinations of the real primaries of monitor 196 that cannot be produced by any combination of the real primaries of LED monitor 296. Specifically, there is no combination of the real primaries of LED monitor 296 that can generate the colors in cross-hatched areas 345 and 355.

Irrespective of the color display limitations of liquid crystal display monitor 296 that is backlit by light emitting diodes, directly mapping the primary color combinations in gamut 395CCFL of monitor 196 to the color combinations in gamut 395LED of monitor 296 enables the color characteristics of monitor 296 to be completely changed so that monitor 296 emulates monitor 196. This mapping effectively copies the primary color combinations of a first monitor to a different second monitor so that identical colors are produced by the two different monitors, when the two different monitors display the same scene. Herein, different monitors have different display technologies. When it is said that a color is mapped, it is the color of a pixel that is mapped, where the pixel includes a plurality of sub-pixels, sometimes referred to a plurality of color components.

Normally, for general purpose monitors a direct mapping of the virtual primaries is not used because the colors are only identical if a requested color of a pixel is within the real/physical gamut of the second monitor. If the requested color is within the gamut of the first monitor and the requested color is within the gamut of the second monitor, the requested color looks identical in both the monitors. If, however, the requested color is within the gamut of the first monitor, but the requested color is outside the gamut of the second monitor, e.g., in one of areas 345 and 355, the requested color does not match across monitors.

Moreover, multiple different combinations of the real primaries of the first monitor, i.e., different colors produced by the first monitor, map to the same combination of virtual primaries, i.e., the same color, for the second monitor because the second monitor cannot display these out-of-gamut requested colors. Having multiple different colors of the first monitor map to the same color of the second monitor is highly undesirable because colors that should appear different would appear exactly the same.

Hence, the concept of a direct mapping of real primaries for a first display technology to virtual primaries for a second display technology is not used for matching color between two general-use display technologies. Rather, several different techniques have been suggested to alleviate the problem of mapping many colors in a first monitor gamut to a single color in a second monitor gamut. However, each of these techniques distorts the colors between the two gamuts to some extent, and so it is not possible to display exactly the same colors on two different display technologies.

However, surgical scenes displayed on CCFL monitor 196 and on LED monitor 296 are different from scenes typically displayed on general-use displays. Surgical display units 195 and 295 are primarily used to display scenes of surgical sites that exist in humans and animals. Such scenes usually do not include any greens or intense blues such as those found in color area 355.

Figure 4:
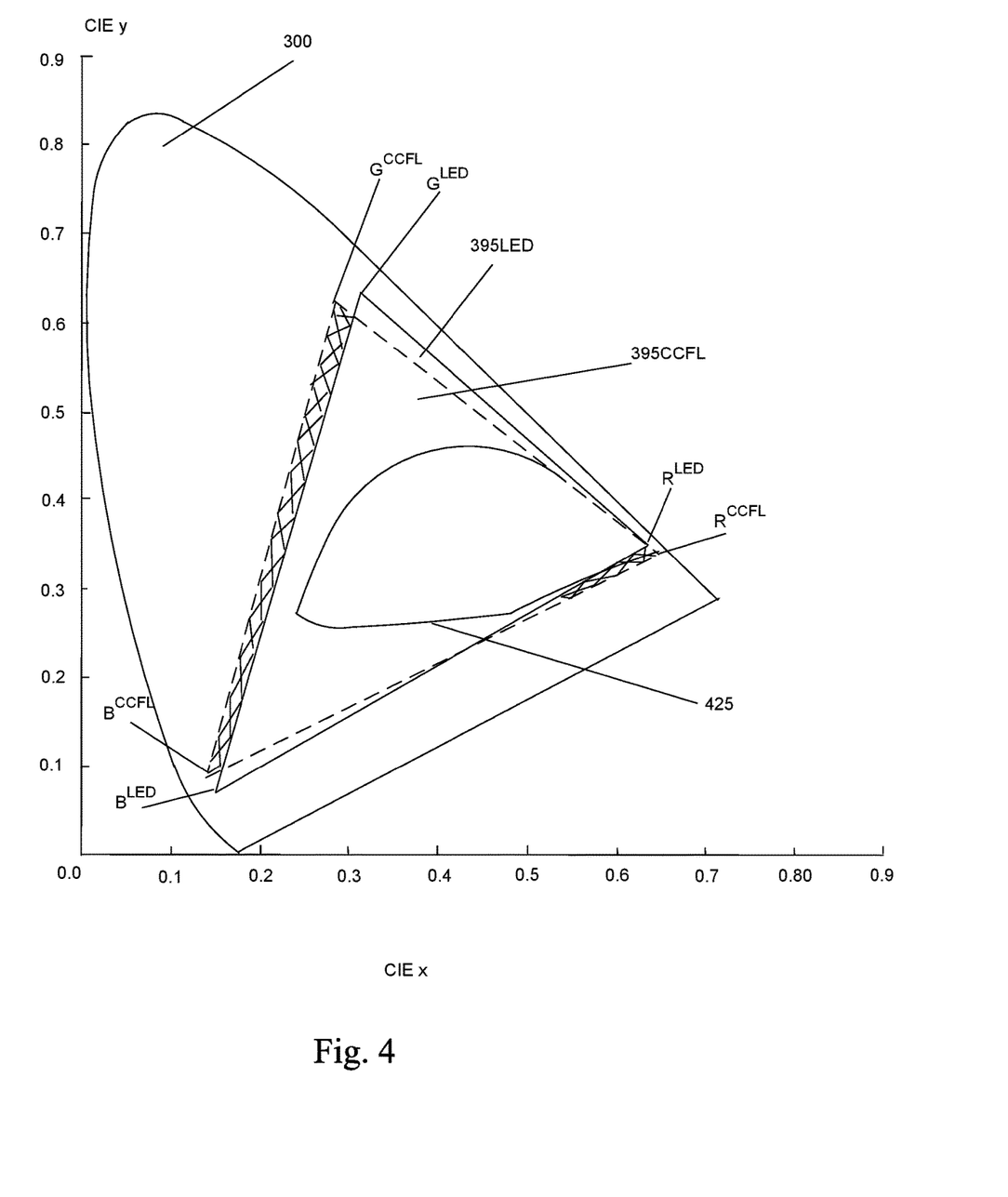
FIG. 4 illustrates the region of the CIE 1931 chromaticity diagram that includes colors found in surgical site scenes.

The colors found in surgical site scenes are what should be keep consistent across different types of monitors, e.g., across monitors using different display technologies. In FIG. 4, curve 425 bounds colors that are typically found in surgical site scenes. As illustrated in FIG. 4, most all the colors found in surgical site scenes are contained in gamut 395LED of display unit 295. While there are some intense reds that cannot be reproduced by LED monitor 296, there are only a small number of such colors, and so this does not noticeably affect the scene displayed by LED monitor 296.

Given that the colors in a surgical site scene are contained in gamut 395LED of monitor 296, the direct mapping of the real primaries of first monitor 196 to virtual primaries of second monitor 296 does not suffer any issues and assures that the same color is displayed on both monitors. In fact, the direct mapping of the real primaries provides the best physical match of surgical colors compared to any other type of approach for in-gamut colors matching across two different display technologies. This direct mapping of real primaries is applicable to any scene that is made up of only colors common to the gamuts of the two different monitors of interest.

In some surgical site scenes, tissue is false colored or other non-surgical graphic overlays are superimposed on a surgical site scene. With direct mapping, the colors used for false coloring and for non-surgical graphic overlays should be selected so that the colors are in the gamuts of both display technologies.

In one aspect, an R, G, B, pixel from imaging pipeline 210 is a gamma corrected pixel, and so can be displayed directly by CCFL monitor 196. However, a gamma corrected color space is not a linear color space. Thus, before virtual primaries transform color controller 220 can perform a mapping of the pixel, the pixel is converted to a linear color space, i.e., $$\begin{bmatrix} R_r^{CCFL} \\ G_r^{CCFL} \\ B_r^{CCFL} \end{bmatrix} = \begin{bmatrix} R^{CCFL} \\ G^{CCFL} \\ B^{CCFL} \end{bmatrix}^{1/\gamma} \quad (1)$$

where $R_r^{CCFL}$, $G_r^{CCFL}$, and $B_r^{CCFL}$ represent three sub-pixels of different real primary colors of monitor 196 in a linear R-G-B color space; and γ is the gamma correction factor, e.g., 2.2.

To map a color of a pixel having three sub-pixels of different real primary colors $R_r^{CCFL}$, $G_r^{CCFL}$, and $B_r^{CCFL}$ to the same color expressed in terms of primaries $X^{CCFL}$, $Y^{CCFL}$, and $Z^{CCFL}$ in the X-Y-Z color space, the following definition is used:

$$\begin{bmatrix} X^{CCFL} \\ Y^{CCFL} \\ Z^{CCFL} \end{bmatrix} = [T_{RGB \rightarrow XYZ}^{CCFL}] * \begin{bmatrix} R_r^{CCFL} \\ G_r^{CCFL} \\ B_r^{CCFL} \end{bmatrix} \quad (2)$$

where $[T_{RGB \rightarrow XYZ}^{CCFL}]$ is a three by three transform that converts a first color pixel in the R-G-B color space of first monitor 196 to the identical color in the X-Y-Z color space.

Thus, expression (2) is a definition of a direct mapping of a color of a pixel in gamut 395CCFL in the R-G-B color space to an identical color of a pixel in X-Y-Z color space. The pixel in X-Y-Z color space is sometimes referred to as a third pixel or an intermediate pixel.

For monitor 296, to map a pixel having three sub-pixels of different real primary colors $R_r^{LED}$, $G_r^{LED}$, and $B_r^{LED}$ to the same color expressed in terms of primaries $X^{LED}$, $Y^{LED}$, and $Z^{LED}$ in the X-Y-Z color space, the following definition is used.

$$\begin{bmatrix} X^{LED} \\ Y^{LED} \\ Z^{LED} \end{bmatrix} = [T_{RGB \rightarrow XYZ}^{LED}] * \begin{bmatrix} R_r^{LED} \\ G_r^{LED} \\ B_r^{LED} \end{bmatrix} \quad (3)$$

where $[T_{RBG \rightarrow XYZ}^{LED}]$ is a three by three transform that converts a first color pixel in the R-G-B color space of second monitor 296 to the identical color in the X-Y-Z color space.

In one aspect, the three by three transforms T in definitions (2) and (3) are empirically determined. For a monitor, a photometer is used to measure the X-Y-Z values coming from the monitor when displaying a red color, a green color, and a blue color. These three sets of X-Y-Z values form transformation matrix T. The first column of transformation matrix T is the X-Y-Z values measured from the displayed red color, the second column of transformation matrix T is the X-Y-Z values measured from the displayed green color, and the last column of transformation matrix T is the X-Y-Z values measured from the displayed blue color.

For two monitors to represent the same color requires their X-Y-Z representations of the color to be equal for all colors:

$$\begin{bmatrix} X^{LED} \\ Y^{LED} \\ Z^{LED} \end{bmatrix} = \begin{bmatrix} X^{CCFL} \\ Y^{CCFL} \\ Z^{CCFL} \end{bmatrix}$$

Substituting the definition of X-Y-Z in expression (3) into this expression gives:

$$[T_{RGB \rightarrow XYZ}^{LED}] * \begin{bmatrix} R_r^{LED} \\ G_r^{LED} \\ B_r^{LED} \end{bmatrix} = \begin{bmatrix} X^{CCFL} \\ Y^{CCFL} \\ Z^{CCFL} \end{bmatrix} \quad (4)$$

or $$\begin{bmatrix} R_r^{LED} \\ G_r^{LED} \\ B_r^{CCFL} \end{bmatrix} = [T_{RGB \rightarrow XYZ}^{LED}] * \begin{bmatrix} X^{CCFL} \\ Y^{CCFL} \\ Z^{CCFL} \end{bmatrix}$$

Expression (4) is a definition of a direct mapping of a color in gamut 395CCFL in the X-Y-Z color space to an identical color of a pixel in display unit 295. The mapping, i.e., transformation, performed by virtual primaries transform controller 220 is obtained by substituting the definition of the pixel in X-Y-Z color space in expression (2) into expression (4), which gives:

$$\begin{bmatrix} R_r^{LED} \\ G_r^{LED} \\ B_r^{LED} \end{bmatrix} = [T_{RGB \rightarrow XYZ}^{LED}]^{-1} * [T_{RGB \rightarrow XYZ}^{CCFL}] * \begin{bmatrix} R_r^{CCFL} \\ G_r^{CCFL} \\ B_r^{CCFL} \end{bmatrix} \quad (5)$$

$$\begin{bmatrix} R_r^{LED} \\ G_r^{LED} \\ B_r^{LED} \end{bmatrix} = [T_{RGBCCFL \rightarrow XYZ \rightarrow RGBLED}] * \begin{bmatrix} R_r^{CCFL} \\ G_r^{CCFL} \\ B_r^{CCFL} \end{bmatrix} \quad (6)$$

where $[T_{RGBCCFL \rightarrow XYZ \rightarrow RGBLED}] = [T_{RGB \rightarrow XYZ}^{LED}]^{-1} * [T_{RGB \rightarrow XYZ}^{CCFL}]$.

Expression (6) defines a direct mapping of a pixel color in gamut 395CCFL to the identical pixel color in gamut 395LED. Unlike other transforms which result in some distortion of the colors in a scene on two different display technologies, with the direct mapping, as described above, the first pixel and the second pixel have identical colors for each pixel in a scene.

Before the pixel defined in expression (6) can be sent to monitor 296, the pixel must be transformed from the linear color space to a gamma corrected color space, i.e., $$\begin{bmatrix} R^{LED} \\ G^{LED} \\ B^{LED} \end{bmatrix} = \begin{bmatrix} R_r^{LED} \\ G_r^{LED} \\ B_r^{LED} \end{bmatrix}^{\gamma} \qquad (7)$$

The direct mapping defined by expression (6) can produce primary color values that are greater than one or less than zero for display unit 295, and these values are simply clipped to one and zero respectively. This clipping would distort an image displayed by a general-use monitor and it is why those of skill in the art would say that this direct mapping is unacceptable. However, for surgical site scenes, colors outside gamut 395LED typically are not encountered and so this direct mapping exactly reproduces the same color in both display technologies. As stated previously, the direct mapping is the only one that does not result in some distortion of the colors in a surgical scene on two different display technologies.

Thus, in one aspect, virtual primaries transform controller 220 implements the direct mapping defined in expressions, (1), (6), and (7). Virtual primaries transform controller 220 maps a color of a first pixel in a surgical site scene received from imaging pipeline 210 to an identical color of a second pixel, which is displayed on LED monitor 296. Again, the first pixel and the second pixel are the same color.

The direct mapping performed by controller 220 assures that the colors of pixels in a surgical site scene displayed using two different display technologies are identical. Thus, each of monitor 196 and monitor 296 displays a surgical site scene and the two surgical site scenes have identical colors throughout the scenes even though monitor 196 and monitor 296 utilize different display technologies. Sometimes, monitor 196 and monitor 296 are referred to as surgical monitors.

Again, the use of surgical monitors and surgical site scenes is illustrative only and is not intended to be limiting. Any scene that has only colors within the gamuts of monitors with different display technologies can be directly mapped, as described above, so that the scenes displayed on the monitors with the different display technologies have identical colors. Alternatively stated, a scene that does not include colors which are outside a region of overlap between gamuts of two different display technologies, e.g., all the colors of the scene are common to the gamuts of the two different display technologies, can be directly mapped, as described above, so that the scenes displayed on the monitors having the different display technologies have identical colors.

Virtual primaries transform controller 220 described above may be implemented in practice by any number of modules and each module may include any combination of components. Each module and each component may include hardware, software that is executed on a processor, and firmware, or any combination of the three. Also, the functions and acts of a virtual primaries transform controller, as described herein, may be performed by one module, or divided up among different modules or even among different components of a module. When divided up among different modules or components, the modules or components may be centralized in one location as illustrated in FIG. 2, or distributed across a computer-assisted surgical system for distributed processing purposes.

In the above examples, a single imaging pipeline has been shown and described. However, in a system that utilizes stereoscopic scenes, a second pipeline identical to the pipelines described above would be used so that one pipeline processed a left captured frame from a left image capture unit, and another pipeline process a right capture frame from a right image capture unit. Repeating the above description for the second pipeline would be redundant, and so is not included herein for clarity.

Herein, a computer program product comprises a medium configured to store computer readable code needed for any one or any combination of methods described herein or in which computer readable code for any one or any combination of the methods is stored. Some examples of computer program products are CD-ROM discs, DVD discs, flash memory, ROM cards, floppy discs, magnetic tapes, computer hard drives, servers on a network and signals transmitted over a network representing computer readable program code. A tangible non-transitory computer program product comprises a medium configured to store computer readable instructions for any one of, or any combination of the methods described herein or in which computer readable instructions for any one of, or any combination of the methods is stored. Tangible non-transitory computer program products are CD-ROM discs, DVD discs, flash memory, ROM cards, floppy discs, magnetic tapes, computer hard drives and other physical storage mediums.

In view of this disclosure, instructions used in any one of, or any combination of methods described herein can be implemented in a wide variety of computer system configurations using an operating system and computer programming language of interest to the user.

As used herein, "first," "second," "third," etc. are adjectives used to distinguish between different components or elements. Thus, "first," "second," and "third" are not intended to imply any ordering of the components or elements or to imply any total number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

I claim:

1. A method comprising:
mapping directly, for each pixel in a scene, a first color of a first pixel of the scene to a second color of a second pixel for display on a second display device having a second display technology, the second color being identical to the first color, the first color of the first pixel being defined by a combination of at least three sub-pixels of first real primary colors of a first display technology, the second color of the second pixel being determined by mapping the first real primary colors of the first display technology to virtual primary colors for the second display technology and forming a combination of at least three sub-pixels of the virtual primary colors to define the second color of the second pixel, the virtual primary colors being different from second real primary colors of the second display technology.

2. The method of claim 1, further comprising:
displaying the second pixel on the second display device.

3. The method of claim 1, wherein the second pixel is part of a surgical scene.

4. The method of claim 1:
wherein the first color of the first pixel is in a gamut of a first display device; and
wherein the second color of the second pixel is in a gamut of the second display device.

5. The method of claim 4, wherein the gamut of the first display device is a gamut of a liquid crystal display monitor backlit with cold-cathode fluorescent tubes.

6. The method of claim 5, wherein the gamut of the second display device is a gamut of a liquid crystal display monitor backlit by light emitting diodes.

7. The method of claim 1, wherein the mapping directly a first color of a first pixel to a second color of a second pixel for display on a second display device having a second display technology comprises:
mapping directly the first color of the first pixel to an identical color of a third pixel in an X-Y-Z color space.

8. The method of claim 7, wherein the mapping directly a first color of a first pixel to a second color of a second pixel for display on a second display device having a second display technology comprises:
mapping directly the color of the third pixel in the X-Y-Z color space to an identical color of the second pixel, the identical color of the second pixel being the second color.

9. The method of claim 8, wherein the mapping directly the color of the first pixel to an identical color of a third pixel in an X-Y-Z color space and the mapping directly the color of the third pixel in the X-Y-Z color space to an identical color of the second pixel are performed together in a single mapping act.

10. A method comprising:
receiving a plurality of pixels comprising a surgical scene, the plurality of pixels including colors each defined as a combination of first real primary colors of a first display technology;
mapping directly, for each pixel of the surgical scene, a first color of a pixel of the scene to a second color of a second pixel to be displayed by a display device having a second display technology, the second color of the second pixel being determined by mapping the first real primary colors of the first display technology to virtual primary colors for the second display technology and forming a combination of the virtual primary colors to define the second color of the second pixel, at least one of the virtual primary colors being outside a gamut defined by second real primary colors of the second display technology; and
displaying the surgical scene on the display device having the second display technology, the displayed surgical scene including the second pixel having the second color, wherein the first color and the second color are a same color.

11. The method of claim 10:
wherein the second color is in the gamut defined by the second real primary colors of the second display technology of the display device; and
wherein the first color is in a gamut defined by the first real primary colors of the first display technology.

12. The method of claim 11, wherein the gamut defined by the first real primary colors of the first display technology is a gamut of a liquid crystal display monitor backlit with cold-cathode fluorescent tubes.

13. The method of claim 11, wherein the gamut defined by the second real primary colors of the second display technology is a gamut of a liquid crystal display monitor backlit by light emitting diodes.

14. An apparatus comprising:
a display unit comprising a virtual primaries transform controller and a display device;
the virtual primaries transform controller being configured to receive a plurality of pixels, the plurality of pixels comprising a scene, a first pixel of the plurality of pixels having a first color defined by a first combination of three sub-pixels of first real primary colors, the virtual primaries transform controller being configured to directly map the first color of the first pixel to a second color of a second pixel, the second color of the second pixel being determined by mapping the first real primary colors to virtual primary colors for the display device and forming a second combination of three sub-pixels of the virtual primary colors to define the second color of the second pixel, the virtual primary colors being different from second real primary colors of the display device, wherein the first color and the second color are a same color; and the display device being coupled to the virtual primaries transform controller, and the display device being configured to receive the second pixel and to display the second pixel.

15. The apparatus of claim 14, wherein the second pixel is part of a surgical scene.

16. The apparatus of claim 14, wherein the virtual primaries transform controller being configured to directly map the first color of the first pixel to a second color of a second pixel comprises:
the virtual primaries transform controller being configured to map directly the first color of the first pixel to an identical color of a third pixel in an X-Y-Z color space.

17. The apparatus of claim 16, wherein the virtual primaries transform controller being configured to directly map the first color of the first pixel to a second color of a second pixel comprises:
the virtual primaries transform controller being configured to map directly the color of the third pixel in the X-Y-Z color space to an identical color of the second pixel, the identical color of the second pixel being the second color.

18. The apparatus of claim 17, the virtual primaries transform controller being configured to map directly the color of the first pixel to an identical color of a third pixel in a X-Y-Z color space and the virtual primaries transform controller being configured to map directly the color of the third pixel in the X-Y-Z color space to an identical color of the second pixel comprises the virtual primaries transform controller being configured to perform a single direct mapping.

19. The method of claim 1, wherein at least one of the virtual primary colors is outside a color gamut defined by the second real primary colors of the second display technology.

20. The method of claim 19, wherein each directly mapped second color for each respective pixel in the scene is within the color gamut defined by the second real primary colors of the second display technology.

21. The method of claim 1, wherein the mapping directly of the first color of the first color to the second color of the second pixel is performed using at least one empirically determined transform matrix.

* * * * *